(12) United States Patent
Gawin et al.

(10) Patent No.: US 6,281,213 B1
(45) Date of Patent: Aug. 28, 2001

(54) AVERSIVE TREATMENT OF STIMULANT ABUSE

(76) Inventors: Frank H. Gawin, 20799 Cool Oak Way, Malibu, CA (US) 90265; Elena Khalsa-Dennison, 17152 Palisades Cir., Pacific Palisades, CA (US) 90272

( * ) Notice: Subject to any disclaimer, the term of this patent is extended or adjusted under 35 U.S.C. 154(b) by 0 days.

(21) Appl. No.: 09/251,002

(22) Filed: Feb. 16, 1999

Related U.S. Application Data

(63) Continuation-in-part of application No. 08/853,162, filed on May 8, 1997, now abandoned.

(51) Int. Cl.⁷ .......................... A61K 31/495; A61K 31/50
(52) U.S. Cl. .......................................................... 514/252.13
(58) Field of Search .......................................... 514/252.13

(56) References Cited

U.S. PATENT DOCUMENTS 5,059,600 * 10/1991 Gawin et al. .

* cited by examiner

Primary Examiner—William R. A. Jarvis

(57) ABSTRACT

Psychomotor stimulant addiction in humans is treated by administering to a human patient before or during a hypodopaminergic "crash" following the psychomotor stimulant induced hyperdopaminergic high or within a period of 3 hours to 21 days prior thereto, a dosage of a pharmaceutically active neuroleptic compound effective to produce aversion to any psychomotor stimulant taken within this period.

11 Claims, No Drawings

AVERSIVE TREATMENT OF STIMULANT ABUSE

This application is a continuation-in-part of U.S. Ser. No. 08/853,162, filed May 8, 1997, now abandoned, entitled Aversive Treatment of Stimulant Abuse.

GOVERNMENT RIGHTS

This invention was made with U.S. Government support. Accordingly, the U.S. Government has certain rights in this invention.

BACKGROUND OF THE INVENTION

1. Field of the Invention

The present invention concerns treating patients suffering from psychomotor stimulant (cocaine, methylphenidate and the amphetamines) and other substance abuse or dependence disorders by administering a pharmaceutically active compound, which results in aversive symptoms when combined with the stimulant.

2. Background Information

One of the most problematic addictive habit disorders is "crack" cocaine molding. "Crack" cocaine smoking has now produced epidemic cocaine dependence in the urban United States, following earlier epidemic abuse in the Bahamas (Jekel, J. F., Allen, D. F., Podlewski, H. Clarke, N. Dean-Patterson, S. Cartwright, P., "Epidemic Cocaine Free-Base Abuse: Case Study from the Bahamas," *Lancet.* (1986), 1, 459, 462).

Cocaine, the amphetamines, and methylphenidate are equivalent in their central effects, in their abuse liability, and in the treatments employed to combat their abuse (Gawin, F. H., Ellinwood, E. H., "Cocaine and Other Stimulants; Actions, Abuse, and Treatment," *New Engl. J. Med* (1988), 318, 1173–1182 and Gawin, F. H., Kleber, H. D., "Evolving Conceptualizations of Cocaine Dependence," *Yale J. Biol. Med.*, (1988) 123–136). Smoking is the most common administration route in severe dependence and abuse, but intravenous, intranasal, oral and other administration routes can all produce abuse and dependence requiring treatment.

"Crack" is defined as cocaine distributed in ready-to-smoke form (cocaine free-base), rather than as the injectable or insufflatable cocaine hydrochloride. Previously, cocaine smoking ("freebasing") required a complex extraction by the end user, of free cocaine base from cocaine hydrochloride, limiting the availability and thus the extent of cocaine dependence by smoking (Gawin and Ellinwood, supra).

"Crack" is generally sold in small, inexpensive one or two inhalation quantities, in a marketing system that, in contrast to prior cocaine distribution, saturates a region with ubiquitous "street" cocaine distributors. The combination of low initial expense, unprecedented availability, and extreme abuse liability has resulted in an epidemic of refractory, recurrent cocaine dependence, making obvious the limits of current cocaine abuse treatment strategies for "crack" abuse, and has lead to unprecedented levels of public concern. Recently, similar epidemic methamphetamine use patterns have also appeared, as has methamphetamine smoking ("crank" or "ice").

Stimulant abstinence is characterized by days to months of dysphoria (Gawin, F. H., Kleber, H. D., "Abstinence Symptomatology and Psychiatric Diagnosis in Chronic Cocaine Abusers," *Arch. Gen. Psychiatry* (1986), 43, 107–113) that produces craving. Episodically and indefinitely thereafter additional pulsatile craving is produced by unpredictable exposures to cues that evoke vivid memories of drug euphoria.

Prior outpatient pharmacotherapy trials for cocaine dependence demonstrate that heterocyclic antidepressants are sometimes effective in enhancing initial attainment of cocaine abstinence, but that their efficacy, as in treatment of depression, is delayed by 10–14 days from the outset of therapy (Giannini, A. J., Malone, D. A., Giannini, M. C., Price, W. A., Louiselle, R. H., "Treatment of Depression in Chronic Cocaine and Phencyclidine Abuse with Desipramine," *J. Clin. Pharmacol.* (1986), 26, 211–4 and Gawin, F. H., Kleber, H. D., Byck, R. Rounsaville, B. Kosten, T. R., Jarlow, P., Morgan, C. "Desipramine Facilitation of Initial Cocaine Abstinence," *Arch. Gen. Psychiatry* (1989) *Arch. Gen Psychiatry,* 46, 117–121). Further, efficacy is not prolonged beyond six weeks of treatment, so only an effect facilitating initial abstinence and none on long-term relapse prevention exists (Carroll, K. M. Rounsaville, B. J., Gordon, L. T., Jatlow, P. M., Nich, C., Bisighini, R. M., and Gawin, F. H., "Psychotherapy and Pharmacotherapy for Ambulatory Cocaine Abusers," *Arch. Gen. Psychiatry* (1994), 51, 177–87). In outpatient "crack" smokers, the extreme availability of the drug often results in resumption of cocaine smoking early in treatment, producing noncompliance to voluntary oral medication regimens that usually results in cessation of all forms of treatment, including psychotherapy, before the possible onset of any therapeutic medication effects (Gawin, Kieber, Byck, Rounsaville, Kosten, Jatlow and Morgan, supra). In this context, 1) a depot long acting preparation would have advantages over other methods of medication administration; 2) more rapidly acting agents are needed and unavailable; and 3) no long term relapse prevention agent exists.

Flupenthixol decanoate is a long acting depot xanthene derivative with unique properties, having both delayed antidepressant activity at low doses (Poldiger, W. Siebems, S., "Depression-inducing and Antidepressive Effects of Neuroleptics: Experiences with Flupenthixol and Flupenthixol Decanoate," Neuropsychobiology (1983), 10, 131–136 and Robertson, M. M., Trimble, M. R. (1982), "Major Tranquilizers Used as Antidepressants," *J. Affective Dis.* 4, 173–195) and immediate neuroleptic activity at higher doses (Trueman, H. R., Valentine, M. G. (1974) "Flupenthixol Decanoate In Schizophrenia," *Br. J. Psychiatry,* 124, 58–59).

Similar to tricyclic antidepressants, it was thought depot flupenthixol decanoate both might positively influence the outcome of the treatment of the habit disorders and obviate compliance problems. However, double-blind studies demonstrating that flupenthixol decanoate significantly improves mood, craving or cocaine use over placebo have not been reported.

Another clinical approach to addictive therapy is the pharmacological production of symptoms of aversion to the agent causing the addiction. This is the basis for disulfiram (antabuse) treatment of alcoholism, which has demonstrated clear rapidly acting efficacy both as an abstinence initiation facilitating treatment and relapse prevention treatment, but predominantly in motivated sub-populations whose use is strongly linked to unpredictable cues. In such cases the craving based on the expectation of stimulant euphoria is reduced or eliminated because aversive symptoms are expected. However, to date, no safe, aversive pharmacological method for psychomotor stimulant (cocaine, the amphetamines or methylphenidate) abuse and dependence that parallels the use of disulfiram ("antabuse") for alcohol abuse has yet appeared. A new, aversive pharmacological interaction between neuroleptics and psychomotor stimulants that leads to therapeutic improvement of stimulant abuse and dependence has been needed.

It is therefore a principal object of the present invention to reduce or eliminate stimulant abuse and dependence in actively using humans, or in patients who have established abstinence of several weeks, to help prevent relapse indefinitely.

SUMMARY OF THE INVENTION

The present invention provides a method for treating psychomotor stimulant addiction in humans. The method consists of administering to a currently abstinent human patient at risk for relapse before or during a hypodopaminergic "crash" following a psychomotor stimulant induced hyperdopaminergic high, for example, within 10–14 days prior thereto, a dosage of a pharmaceutically active neuroleptic compound effective to produce aversion to any psychomotor stimulant taken within a period of 3 hours to 21 days following administration of the neuroleptic compound. In the case of depot, long-acting forms of the compound, the period is 7–21 days. In the case of oral forms, the period is 3 hours to 2 days. Taking a psychomotor stimulant during this period results in strongly aversive extrapyramidal symptoms (EPS). Therapy is most effective when the neuroleptic compound is administered in conjunction with education and counseling of the patient as to the expected aversive symptoms to be experienced by the patient upon taking a stimulant while an effective concentration of neuroleptic is present.

The method of the present invention comprises administering a pharmaceutically active neuroleptic compound, such as flupenthixol, to a currently abstinent human patient at risk for relapse, who has been informed that breaking abstinence at any time within a period of 21 days after being administered the depot neuroleptic compound, or a period of 2 days after being administered the oral neuroleptic compound will cause aversive extrapyramidal symptoms. The dosage of neuroleptic compound is that dosage which produces aversive extrapyramidal symptoms upon taking a psychomotor stimulant such as cocaine within 21 days of administration of the depot neuroleptic or within 2 days of administration of the oral euroleptic.

Thus, the method consists of administering both a psychotherapeutic statement and a dosage of a pharmaceutically active neuroleptic compound sufficient to result in aversive extrapyramidal symptoms upon taking a psychomotor stimulant within 21 days of administering the depot neuroleptic or 2 days of the oral form.

For example, typically a cocaine binge lasts 6 to 18 hours. A hyperdopaminergic high is induced by such cocaine binge, followed by a hypodopaminergic crash, which lasts about 3–6 hours. If a depot form of flupenthixol is administered to the patient and the patient is told that, for the next 21 days, if cocaine is taken by the patient, aversive extrapyramidal symptoms will occur, the patient will continue abstaining from cocaine rather than risk the extremely unpleasant aversive extrapyramidal symptoms. Patients who reached the stage of abstinence consolidation for 10 or more days of continuous abstinence will prolong their abstinence further rather than risk the aversive extrapyramidal symptoms resulting from breaking abstinence.

Thus, the method of the present invention comprises the administration of both a prior psychotherapeutic statement informing the addict they are being administered medication which will result in an aversive interaction if cocaine is also administered, and a dosage of a flupenthixol salt or ester effective to cause aversive extrapyramidal symptoms upon interaction with cocaine taken within 3 hours to 21 days of administering a depot form of flupenthixol, which is administered at a time within 21 days prior to the 3–6 hour period of hypodopaminergic crash following the hyperdopaminergic high induced by a typical 6 to 18 hour cocaine binge.

Actual evocation of the aversion in the clinical setting may not be uniformly necessary. In other instances it may be desirable to ascertain aversive extrapyramidal symptoms experience by administration of the flupenthixol or other neuroleptic during the hypodopaminergic "crash." The method in this instance comprises subsequently administering a pharmaceutically active neuroleptic compound in a dosage effective to rapidly produce aversive extrapyramidal symptoms upon interaction with a subsequently administered psychomotor stimulant. In a preferred embodiment, flupenthixol decanoate administered intramuscularly at dosages of 0.015–6 mg/kg is used to produce 3 hours to 21 days aversion to stimulants. In a short-acting embodiment, flupenthixol hydrochloride administered orally at dosages of 0.5–3.0 mg is used to produce 3 hours to 2 days aversion.

DESCRIPTION OF THE PREFERRED EMBODIMENTS

Previous study of neuroleptics and stimulants has focused on (1) antistimulant withdrawal effects of low, antidepressant doses of flupenthixol, or (2) the acute blockade of stimulant effects:

1. Antidepressant doses of flupenthixol have been proposed as a method to decrease the dysphoric withdrawal period that occurs on abstinence from stimulants. That use involves possible amelioration of negative symptoms and normalization of subsensitive reward systems, and has not demonstrated clinical efficacy in controlled clinical trials. It does not involve any acute interaction between the neuroleptic and acute stimulant effects, and is not based on the motivational power of avoiding strongly aversive symptoms.

2. Extensive preclinical research has explored neuroleptics and stimulants to elucidate mechanisms of reward (Gawin, F. G., Humblestone, B. G., and Allen, D. F., U.S. Pat. No. 5,059,600, Oct. 22, 1991), but none have focused on aversive extrapyramidal symptoms. Such research demonstrates that neuroleptics block D-2 and other dopamine receptors, that acute stimulant administration produces euphoria (as do other abused agents) by increasing intrasynaptic dopamine concentrations (Gawin, F. G., "Cocaine Addition: Psychology and Neurophysiology", *Science*, 251, 1580–1586, 1991), and that high neuroleptic doses block acute stimulant reward effects in animals (Koob, G. F., Bloom, F. E., "Cellular and Molecular Mechanisms of Drug Dependence", Science, 242 (479), 715–723, 1988). This use of neuroleptics involves the reversal of stimulant effects, not the induction of an aversive state. Hope recently existed that reversal noted in animals would extend to clinical use in humans abusing stimulants. However, clinically tolerable doses of neuroleptics do not block stimulant euphoria in human clinical observations or human laboratory experiments (Sherer, M., Kumor, K., and Jaffe, J., "Effects of Intravenous Cocaine Are Partially Attenuated by Haloperidor", *Psychiatry Res.*, 27 (2), 117–125, 1989). Neuroleptic doses which might be high enough to block euphoria in humans produce persistent debilitating clinical side effects (without stimulant co-administration) and are not clinically tolerated, since doses substantially amplify the stimulant's principal withdrawal symptoms, anhedonia and dysphoria, decimate patient compliance, and are often counter-therapeutic, increasing craving for stimulant (which would temporarily counteract these symptoms). Since blocking doses of neuroleptics did not provide a clinically practical blocking of stimulant euphoria in humans, investigations for this purpose have been abandoned.

EPS reactions to neuroleptics alone have been extensively described as an unwanted side effect in modest to high dosage use in psychiatric disorders. No description of any therapeutic utility of EPS side effects has previously occurred in this or any other context. While EPS has sometimes been reported as a complicating factor in human pharmacology experiments in which neuroleptics are administered with stimulants, it has only been considered as an unwanted, complicating side effect. The potential therapeutic utility of EPS is thus non-obvious and has not been previously noted.

While the acute induction of EPS reactions via adding a second EPS inducing agent in subthreshold (for EPS) neuroleptic treatment is theoretically straightforward, and EPS should be induced by superimposing any treatment (e.g., reserpine) which further suppresses dopaminergic activity on sub-threshold neuroleptic effects, no clinical disorder potentially benefiting from such an interaction has been previously described.

EPS may be inducible very soon after the stimulant induced hyperdopaminergic high ceases, during the rebound, hypodopaminergic crash. The post-stimulant "crash," which is analogous to the alcohol "hangover," occurs in the hours immediately after a stimulant binge, before sleep, usually lasting less than twelve hours. The crash reflects compensatory decreases in dopaminergic transmission in dopaminergic reward pathways due to the preceding stimulant binge, but rarely, if ever, reduces transmission in dopaminergic motor pathways enough to alone produce EPS. The decreased dopamine efflux occurs as a secondary consequence of the prior stimulant induced dopamine re-uptake blockade and transiently high intrasynaptic dopamine concentration with markedly increased dopaminergic transmission, due to excessive intrasynaptic dopamine reactability and degradation during the high. Decreased dopaminergic transmission in motor pathways produces extrapyramidal symptoms (EPS) in Parkinson's disease and as a major side effect of psychiatric neuroleptic treatment. The stimulant crash alone is not associated with EPS. However, sub-threshold predisposition to EPS can be induced by low-dose neuroleptic treatment that is clinically tolerable, and the further decrement to dopaminergic activity occurring with the crash could then be sufficient to produce EPS and render the stimulant substantially aversive.

Nonlimiting examples of pharmaceutically active compounds for use in the present invention include the following:

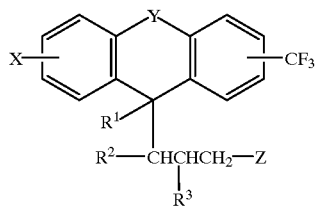

, wherein x is hydrogen, a halogen, $SO_2N(CH_3)_2$ or $CF_3$, Y is a member selected from the group consisting of sulfur and oxygen; R1 and R2 are members selected from the group consisting of hydrogen and hydroxy and, when taken together, a single bond, R3 is a member selected from the group consisting of hydrogen and methyl; and Z is a member selected from the group consisting of di-lower alkylamino, di-lower alkyamino wherein one or both alkyl groups are substituted with hydroxy, N-pyrrolidinyl, N-piperidyl, N-lower alkyl-N-piperazinyl and N-lower-alkyl-N-piperazinyl, wherein the alkyl can be substituted with OH;

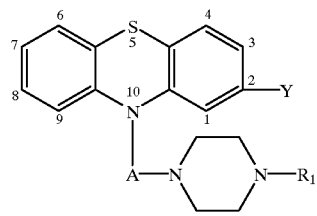

in which Y is perfluoroalkyl of 1 to 3 carbon atoms; A is an alkylene chain of from 2 to 6 carbon atoms separating the nitrogen atoms linked thereto by at least two carbon atoms, and R1 is a member selected from the group consisting of cycloalkyl-lower-alkyl, the cycloalkyl portion having 5 to 6 carbon atoms and the lower-alkyl portion having 1 to 4 carbon atoms, lower alkenyl having 3 to 6 carbon atoms, hydroxy-lower-alkyl having 2 to 6 carbon atoms in the alkyl portion, hydroxy-lower alkyloxy-lower-alkyl, the lower alkyl portions having 2 to 6 carbon atoms in the alkyl portion, lower-alkanoyl having I to 6 carbon atoms, cycloalkyl-lower-alkanoyl, the cycloalkyl portion having 5 to 6 carbon atoms and the lower alkanoyl portion having 2 to 4 carbon atoms, phenyl-lower alkanoyl, the lower alkanoyl portion having 2 to 4 carbon atoms, benzoyl, carbomethoxy, carbethoxy, carbobenzoxy, carbamyl, dialkyl-carbamyl having 1 to 6 carbon atoms in the alkyl portions, N-phenyl-carbamyl, lower alkanoyloxy-lower-alkyl, the lower-alkanoyloxy portion having 2 to 6 carbon atoms and the lower-alkyl portion having 2 to 6 carbon atoms and benzoyloxy-lower-alkyl having 2 to 6 carbon atoms in the lower alkyl portion;

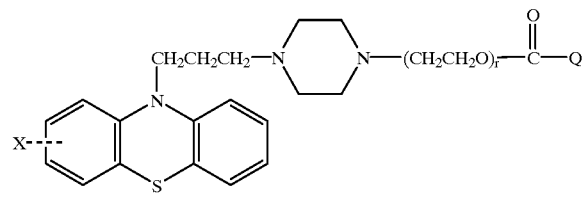

, wherein r is a positive integer from one to 2, X is chloro or trifluoromethyl, Q is a higher alkyl of 6 to 14 carbon atoms, a higher alkenyl of 6 to 14 carbon atoms, a higher alkynyl of 6 to 14 carbon atoms, tolyl, dimethylbenzyl, anisyl or

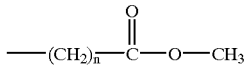

wherein n is a positive integer from 7 to 12.

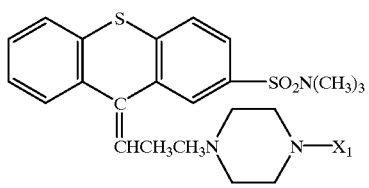

wherein $X_1$ is selected from the group consisting of methyl, 2-hydroxyethyl, 3-hydroxypropyl, dimethylsulfonamido, and methylsulfonyl;

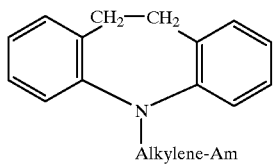

wherein alkylene represents an alkylene chain of 2–3 carbon atoms and Am represents a member selected from the group consisting of a lower molecular alkylamino radical, a low molecular dialkylamino radical, the N-piperidino-N-morpholino-, and N-pyrrolidino radicals;

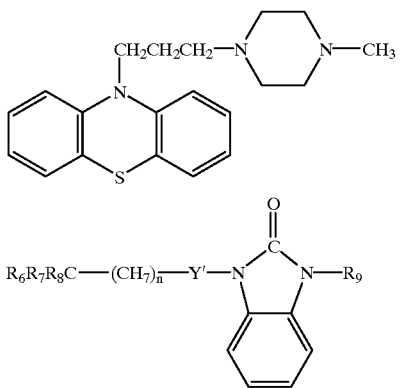

, wherein n is an integer from 2 to 5, $R_6$ is selected from the group consisting of hydrogen, hydroxy, cyano, carbonyl and lower-alkyl-carbamyl, $R_7$ is aryl, $R_8$ is selected from the group consisting of aryl and arylmethylene, R9 is selected from the group consisting of hydrogen, lower alkyl, lower-alkyl-carbonyl, lower-alkoxy-lower-alkyl, hydroxy-lower-alkyl, lower-alkoxy-carbonyl-lower alkyl, lower-alkyl-carbonyl-lower-alkyl, amino-lower-alkyl and halo-lower-alkyl, and $Y_1$ is selected from the group consisting of

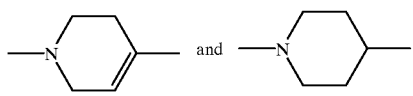

the nitrogen atom of which is attached to the $R_6R_7R_8C$—$(CH_2)n$— moiety; the lower alkyl and lower alkoxy having from 1 to 5 carbon atoms and the aryl being a member of the group consisting of phenyl, halophenyl, lower alkylphenyl, lower alkoxyphenyl, trifluoromethylphenyl, and thienyl;

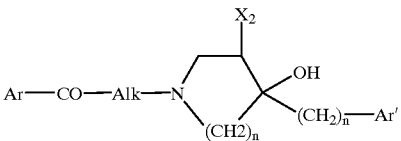

wherein Ar is a member selected from the group consisting of halophenyl, tolyl, methoxyphenyl, dimethoxyphenyl, trimethoxyphenyl, ethoxyphenyl, xylyl, and (lower) alkylphenyl. $Ar^1$ is a member selected from the group consisting of phenyl, halophenyl, methoxyphenyl, dimethoxyphenyl, trifluoromethylphenyl, and (lower) alkylphenyl, Alk is trimethylene, $X_2$ is hydrogen or methyl, n is a positive integer smaller than three, and m is zero, one or two;

11-basic substituted dibenzoxazepines having the formula:

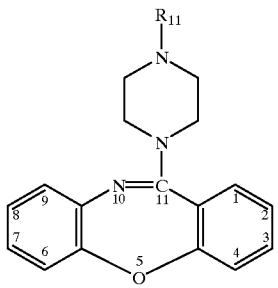

wherein $R_{11}$ is a member selected from the group consisting of hydrogen, lower alkyl, lower hydroxyalkyl, acetylated lower hydroxyalkyl, and alkoxyalkyl having not more than 5 carbon atoms;

derivatives thereof substituted in the benzene nuclei by at least one member selected from the group consisting of halogen, trifluoromethyl, lower alkyl, lower alkoxy, and lower alkylthio;

11-basic substituted dibenzoxazepines having the formula:

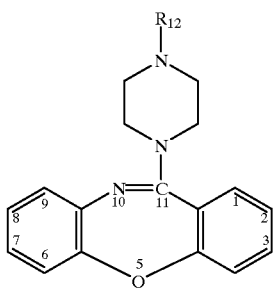

wherein $R_{12}$ represents a member selected from the group consisting of hydrogen, allyl, alkyl containing not more than 3 carbon atoms, hydroxyalkyl containing not more than 3 carbon atoms, alkoxyalkyl containing not more than 6 carbon atoms and alkoyloxyalkyl containing not more than 6 carbon atoms, R13 is a member selected from the group consisting of nitro, amino, aminosulphonyl of the formula $SO_2NR_{14}R_{15}$ wherein $R_{14}$ and $R_{15}$ are the same or different members of the group consisting of hydrogen and methyl, alkyl-sulphinyl of the formula —$SOR_{16}$ wherein $R_{16}$ is alkyl with not more than 3 carbon atoms, and alkylsulphonyl of the formula—$SO_2R_{17}$; wherein $R_{17}$ is alkyl with not more than 3 carbon atoms;

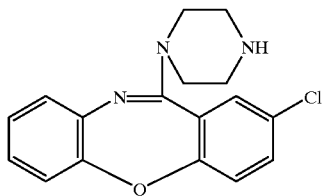

; and 1-$R_{18}$-2-$R_{19}$-3-$R_{20}$-4-oxo-8-$R_{21}$-1,3,8-triaza-spiro (4,5) decane, wherein $R_{18}$ is phenyl, lower alkaryl, lower alkyl, lower alkoxyphenyl, cyclobutyl, cyclopentyl, cyclohexyl, or halophenyl, $R_{19}$ is hydrogen or lower alkyl; $R_{20}$ is hydrogen, hydroxymethyl, lower alkyl, lower-alkylcarbonyl, cyanoethyl, lower alkoxymethyl, lower alkoxycarbonyl-lower alkyl, carbamoyl-lower alkyl, cyclopropylcarbonyl, benzyl, or benzoyl; $R_2$, is (R''')(R''') CH - or Z''' (CH2)$_p$, wherein R''' is methyl or ethyl, R'''' is aryl, arylmethylene or arylethylene, p is a positive integer from 1 to 5, and Z''' is hydrogen, lower alkyl, hydroxy, hydroxy-lower alkoxy, phenyl, diphenyl-cyano-methylene, diaryl-hydroxymethylene, diphenylpropionyl-methylene fluorophenyl-methylene, fluorophenyl-hydroxymethylene, aryloxy, 1,4-benzodioxanyl, halo-1,4-benzodioxanyl, thienyl, halophenyl, lower alkyphenyl, pyridyl, di-lower alkyphenyl, phenyl-lower alkylene, lower alkoxyphenyl, cyclopropylethylenyl, benzoyl, halobenzoyl, thienoyl, lower alkylbenzoyl, lower alkoxybenzoyl, benzoyloxy, benzyloxy, phenylmethoxymethylene, phenylhydroxymethylene, fluorophenyl-lower alkylcarbonyl-oxy-methylene, fluorophenyl-lower alkylene, aryl-lower alkyl arylcyclopropyl, arylthio or (aryl)($R^{10}$)CH—, wherein $R^{10}$ is lower alkyl, aryl, and aryl-lower alkyl, (aryl)$_2$—CH—O—, (lower alkyl)$_2$C—CH— or (aryl)($R^{12}$)C=CH—, wherein $R^{12}$ is hydrogen, lower alkyl, aryl, or aryl-lower alkyl, the lower alkyl and lower alkoxy containing from 1 to 6 carbon atoms and the aryl being phenyl, halophenyl, lower alkylphenyl, lower alkoxyphenyl, trifluoromethylphenyl or 2-thienyl.

Preferred compounds for use in the present invention include the following:

| Compound | Formula | Patent Reference |
|---|---|---|
| pimozide | | French M3695<br>U.S. Pat. No. 3,196,157 |
| fluspirilene | | U.S. Pat. No. 3,238,216 |
| haloperidol | | U.S. Pat. No. 3,438,991 |

-continued

| Compound | Formula | Patent Reference |
|---|---|---|
| loxspine | 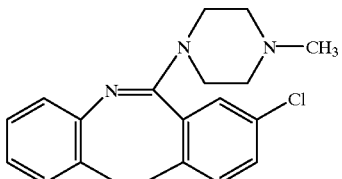 | U.S. Pat. No. 3,546,226<br>U.S. Pat. No. 3,412,193 |
| amoxapine | 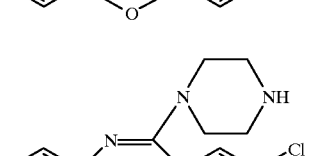 | U.S. Pat. No. 3,663,696 |
| pifluthixol (= 6-fluoro-flupethixol) | | |

Also useful in the method of the present invention are the pharmaceutically acceptable salts of the pharmaceutically active compounds disclosed above and, if applicable, pharmaceutically acceptable esters thereof The entire contents of the above-listed patents are hereby incorporated by reference.

The pharmaceutically active compounds of the present invention can exist as optical isomers and both racemic and diastereomeric mixtures of these isomers which may exist for certain compounds, as well as the individual optical isomers are all within the scope of the present invention. While the racemic mixtures can be separated into their individual isomers through well-known techniques such as, for example, the separation of diastereomeric salts formed with optically active adjuncts, e.g., acids or bases followed by conversion back to the optically active substrates; in most instances, for the compounds of the present invention, the preferred optical isomer can be synthesized by means of stereospecific reactions, beginning with the appropriate stereoisomer of the desired starting material.

As indicated above, the present invention also pertains to pharmaceutically acceptable non-toxic salts of these compounds, containing, for example, NA+, Li+, K+, Ca++, and Mg++. Such salts may include those derived by combination of appropriate cations such as alkali and alkaline earth metal ions or ammonium and quaternary ammonium ions. Metal salts can be prepared by reacting the metal hydroxide with a compound of this invention. Examples of metal salts which can be prepared in this way are salts containing Li+, Na+, K+. A less soluble metal salt can be precipitated from the solution of a more soluble salt by addition of the suitable metal compound. In addition, salts may be formed from acid addition of certain organic and inorganic acids, e.g. HCl, HBr, $H_2SO_4$ or organic sulfonic acids. Finally, it is to be understood that the pharmaceutically active compounds for use in the present invention in their un-ionized, as well as zwitterionic form, and/or in the form of solvates are also considered part of the present invention.

Pharmaceutically acceptable esters of compounds for use in the invention containing OH groups can also be utilized in this invention. Such esters can be prepared by esterification of the OH groups with, for example, carboxylic acids, sulfonic acids, or phosphoric acid. Carboxylic acid esters derived from $C_1$–$C_{10}$-alkylcarboxylic acids, unsubstituted or substituted benzoic acids or $C_1$–$C_6$-alkyl sulfonic acids are nonlimiting examples of acids which can be employed to produce esters for use in this invention.

It is preferred that the pharmaceutically active compound for use in the present invention be formulated into pharmaceutical preparations. Such preparations are composed of one or more of the compounds for use in the present invention in association with a pharmaceutically acceptable carrier. The reference *Remington's Pharmaceutical Sciences,* 7th Edition, A. R. Gemnaro, editor (Mack Publishing Co., 1985), discloses typical carriers and methods of preparation.

The pharmaceutically active compound described for use in the present invention can be administered topically or systemically to humans. By systemic administration is intended, oral, rectal, buccal, nasal and parenteral (i.e., intramuscular, intravenous and subcutaneous) routes. Generally it will be found that when the pharmaceutically active compound is administered orally, a larger quantity of the pharmaceutically active compound is required to produce the same effects as the smaller quantity given parenterally. In accordance with good clinical practice, it is preferred to administer the pharmaceutically active compound at a concentration level that will produce effective antihabitual effects without causing any harmful or untoward side effects and without resulting in a neuroleptic effect in the patient.

Therapeutically, the pharmaceutically active compound is preferably administered as a pharmaceutical composition comprised of an effective anti-habitual amount of the pharmaceutically active compound or a pharmaceutically acceptable salt thereof or an ester thereof and a pharmaceutically acceptable carrier, as stated herein. Pharmaceutical compositions for effecting such treatment will contain a major or minor amount, e.g., from 95 to 0.5% of the pharmaceutically active compound in combination with a pharmaceutical carrier, the carrier comprising one or more solid, semi-solid, or liquid diluents, fillers and formulation adjuvants which are nontoxic, inert, and pharmaceutically acceptable. Such pharmaceutical compositions are preferable in dosage unit form, i.e., physically discrete units containing a predetermined amount of the drug corresponding to a fraction or multiple of the dose which is calculated to produce the desired therapeutic response. Other therapeutic agents can also be present.

Pharmaceutical compositions providing from about 1 to 50 mg of the pharmaceutically active compound per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch) and wetting agents (e.g., sodium lauryl sulfate). Solutions or suspensions of the pharmaceutically active compound with conventional pharmaceutical vehicles are employed for parenteral compositions, such as an aqueous solution for intravenous injection or an oily suspension for intramuscular injection. Such compositions having the desired clarity, stability, and adaptability for parenteral use are obtained by dissolving from 0.1% to 10% by weight of the pharmaceutically active compound in water or a vehicle comprising a polyhydric aliphatic alcohol, such as glycerine, propylene glycol and polyethylene glycol, or mixtures thereof. The polyethylene glycols comprise a mixture of nonvolatile, usually liquid, polyethylene glycols which are soluble in both water and organic liquids and have molecular weights from about 200 to 1500.

On the basis of testing, an intramuscular effective dose of the pharmaceutically active compound, e.g., flupenthixol, could be expected to be from about 2 to about 80 mg weight with about 2 to 60 mg, a preferred dosage range. For pifluthixol, an intramuscular effective dose could be expected to be 1 to 20 mg, preferably 1 to 10 mg, such dose to be administered every 10 to 20 days. For clinical applications, however, the dosage and dosage regimen in each case should be carefully adjusted, utilizing sound professional judgment and consideration of the age, weight and condition of the recipient, the route of administration and the nature and gravity of the stimulant abuse or craving. The dosage may vary based on the medical status of the recipient, e.g., dosages may have to be decreased in cases of impaired metabolism or increased in cases of enhanced metabolism. In some instances, a sufficient therapeutic effect can be obtained at lower doses, while in others, larger doses will be required.

The present invention can be employed to treat humans suffering from stimulant addiction or abuse. Nonlimiting examples of abuse disorders which can be treated by the present invention include the following:

(1) cocaine addiction, abuse or dependency, including addiction to "crack" (cocaine in ready-to-smoke form), injectable cocaine and cocaine taken by nasal inhalation;

(2) addiction to, abuse of or dependency on amphetamines and other stimulants, e.g., methamphetamine and methylphenidate;

(3) addiction to, abuse or dependency on PCP (phencyclidine, "angel dust");

(4) addiction to, abuse of or dependency on stimulant-hallucinogens, e.g., MDA, MDMA, TMA and others;

Certain components of the pharmacology of the pharmaceutically active compounds described for use in this invention, e.g., flupenthixol, particularly their interaction with monoaminergic pathways in discrete brain areas, provide a rationale for the role of the active compound, e.g., flupenthixol, in antagonizing substance addiction in general. Continued overindulgence or inappropriate consumption of foods, as well as habitual use of other addictive substances, such as alcohol, relies in part on "craving." In subjects suffering from substance addictions, "craving" is more of a subjective demand for the addictive substance. The interactions of the active compound, e.g., flupenthixol with monoaminergic transmission in brain regions associated with reward and motor activity appear to result in reducing craving by rendering the experience of intoxication at least partially aversive.

EXAMPLE

The interaction has been observed in ten active stimulant abusers after acute stimulant use while maintained on neuroleptic treatment. Six "crack" cocaine and one methamphetamine user were given the neuroleptic flupenthixol in depot intramuscular preparations. In three other intravenous cocaine or "crack" users, oral administration of haloperidol (n=2.5 mg and 20 mg po) or chlorpromazine (200 mg) occurred. On using "street" stimulants during neuroleptic treatment, these ten patients experienced debilitating, extremely severe but transient akathisia and other extrapyramidal symptoms (EPS) during the "crash" period immediately after the stimulant "high," which later resolved completely and without any evident neuromotor after-effects. The extremely unpleasant but transient akathisia and extrapyramidal symptoms occurred in patients maintained on otherwise well-tolerated (when not using drugs) low dose neuroleptics. In every case, the symptoms occurred only during the acute post-stimulant "crash" immediately following a binge of stimulant use. In all cases, further stimulant use ceased as long as patients perceived that the neuroleptic interaction might persist.

These ten patients all met DSM-IV criteria for stimulant abuse and dependence, but not for other abused substances. In the one patient who received oral PRN chlorpromazine and two receiving oral PRN haloperidol, treatment was intended for severe paranoia after stimulant use. The remaining seven were treated within ongoing clinical trials using long-acting (10–14 days) intramuscular flupenthixol decanoate at low dosages (0.05–0.10 mg/kg/wk) for mood and craving effects.

All these patients showed extremely unpleasant akathisia and other extra-pyramidal symptoms (EPS) at low to moderate, clinically tolerable neuroleptic doses, but only during the stimulant crash. In each case, these symptoms never occurred before neuroleptics with stimulant use alone, were not present in the neuroleptic medicated patients before the episode of re-use of stimulants, and resolved completely, lasting only as long as the crash mood effects did, or until anti-EPS medication was administered. Plasma flupenthixol levels averaged twice those in unaffected patients, indicating somewhat larger or moderate but not high doses could produce clinically useful aversive interaction without other side effects.

Of paramount significance, none of these patients used stimulants again during the neuroleptic treatment. Their experience of akathisia was described as among the worst somatic sensations they had ever experienced, surpassed only by severe pain. In five of these cases (all flupenthixol), akathisia was observed and confirmed by emergency room or substance abuse treatment staff, while the remainder were self-reports provided at the next clinical contact, after the akathisia resolved (none of these patients came into contact with each other).

The non-flupenthixol patients discontinued oral neuroleptics immediately, reporting being uncertain about their ability to cease stimulant use and fearing EPS if they relapsed. The flupenthixol patients all ceased stimulant use, despite mean use of over $300/week and 5/7 days/week of use preceding the EPS, during the one to two weeks that they were aware the intramuscular flupenthixol decanoate remained active.

The cases reported here confirm that modest doses of neuroleptics which, alone, are not associated with side effects, might regularly produce aversive interactions upon superimposed stimulant administration, and that such interactions appear to be safe, reversible, and therapeutically useful. This usage is distinct from prior usage of lower dose flupenthixol as an antiwithdrawal agent (Gawin, F. H., Khalsa, M. E., Brown, J. L., Jatlow, P., "Flupenthixol and Desipramine Treatment of Crack Users: Initial Double-Blind Results", *NIDA Res. Mon.* 132, p. 139, L. Harris, ed., U.S. Department of Health and Human Sciences, NIH Publication No. 93-3505, 1993), or of attempts to use neuroleptics as stimulant blockers (Sherer et al., supra; Gawin et al., supra). These observations likely indicate that (1) the extrapyramidal symptoms reported were unmasked by superimposing pre-synaptic decreases in dopaminergic transmission associated with stimulant "crashing" on decreased nigrostriatal dopaminergic function caused by neuroleptic induced post-synaptic D2 dopamine receptor blockade, but it cannot be ruled out that (2) stimulant administration potentiated the neuroleptic dose-response purely via an acute pharmacodynamic interaction (Kornak, E. P., Eng, F., Hormozdi, S., Cuadra, A., Broderick, P. A., "Flupenthixol Blocks Cocaine-Induced Accumbers Dopamine Release and Concurrent Cocaine Dysfunctional Behavior," *Soc. Neurosci. Abstr.*, Vol. 9(3), p. 1862, 1993) that may be partially or completely independent of changes in dopamine transmission associated with the crash, or that (3) other unknown mechanisms may be responsible.

It will be appreciated that the description and disclosure in the instant specification are set forth by way of illustration and not limitation, and that various modifications and changes may be made without departing from the spirit and scope of the present invention.

What is claimed is:

1. A method for treating psychomotor stimulant addiction comprising:

administering a pharmaceutically active neuroleptic compound to a currently abstinent human patient at risk for relapse;

said patient having been informed that said neuroleptic compound will produce aversive extrapyramidal symptoms upon breaking abstinence by administration of a psychomotor stimulant during the period from administering said compound up to about 21 days thereafter during which time there occurs a hypodopaminergic crash following a hypodopaminergic high induced by administration of said psychomotor stimulant;

said neuroleptic compound being administered in a dosage sufficient to cause production of said aversive extrapyramidal symptoms upon administration of said psychomotor stimulant.

2. A method for treating psychomotor stimulant addiction in a currently abstinent human patient at risk for relapse which comprises the administration of both:

a psychotherapeutic statement informing the addict they are being administered medication which will produce an aversive interaction if psychomotor stimulants are also administered; and an aversion producing dosage of a pharmaceutically active neuroleptic compound.

3. A method for treating cocaine addition in a human patient at risk for relapse after abstinence consolidation which comprises the administration of both:

a prior psychotherapeutic statement informing the addict they are being administered medication which will produce an aversive interaction if cocaine is also administered; and a dosage of a flupenthixol salt or ester effective to produce aversive extrapyramidal symptoms upon interaction with the effects of cocaine taken within 3 hours to 21 days of administering said flupenthixol salt, said salt being administered, at a time within up to 21 days prior to the 3–6 hour period of hypodopaminergic crash following the hyperdopaminergic high induced by a typical 6 to 18 hour cocaine binge.

4. The method of claim 1 wherein said neuroleptic compound is flupenthixol decanoate and said dosage is 0.015 mg/kg to 6 mg/kg administered intramuscularly.

5. The method of claim 1 wherein said neuroleptic compound is flupenthixol salt and said dosage is 0.5 mg to 30 mg given orally.

6. The method of claim 3 wherein said flupenthixol salt or ester is a depot form of flupenthixol and said dosage is effective to produce aversive extrapyramidal symptoms upon interaction with cocaine taken within 3 hours to 21 days of administering said depot form of flupenthixol.

7. The method of claim 3 wherein said depot form of flupenthixol is flupenthixol decanoate.

8. The method of claim 3 wherein said flupenthixol salt or ester is an oral form of flupenthixol and said dosage is effective to produce aversive extrapyramidal symptoms upon interaction with cocaine taken within 3 hours to 2 days of administering said oral form of flupenthixol.

9. The method of claim 8 wherein said oral form of flupenthixol is flupenthixol hydrochloride.

10. The method of claim 1 wherein the dosage of neuroleptic compound constitutes a clinically tolerable dosage effective to induce subthreshold predisposition to extrapyramidal symptoms which, upon decrement to dopaminergic activity occasioned by said crash, will result in the production of extrapyramidal symptoms and render said stimulant substantially aversive.

11. The method of claim 3 wherein said psychotherapeutic statement includes the information that said medication will produce a predisposition to extrapyramidal symptoms such that the onset of said crash will result in extrapyramidal symptoms and substantial aversion to cocaine.

* * * * *